United States Patent [19]

Bradford et al.

[11] 4,023,933

[45] May 17, 1977

[54] PROTEIN-ASSAY REAGENT AND METHOD

[75] Inventors: Marion M. Bradford; William L. Williams, both of Athens, Ga.

[73] Assignee: University of Georgia, Athens, Ga.

[22] Filed: June 10, 1976

[21] Appl. No.: 694,668

[52] U.S. Cl. .............................. 23/230 B; 252/408
[51] Int. Cl.² ........................................ G01N 33/16
[58] Field of Search ................... 23/230 B; 252/408

[56] References Cited

UNITED STATES PATENTS

| | | | |
|---|---|---|---|
| 2,897,058 | 7/1959 | Galat | 23/230 B |
| 3,873,272 | 3/1975 | Wakefield et al. | 23/230 B |
| 3,884,637 | 5/1975 | Gindler | 23/230 B |
| 3,936,271 | 2/1976 | Statter | 252/408 |

*Primary Examiner*—Robert M. Reese
*Attorney, Agent, or Firm*—Oblon, Fisher, Spivak, McClelland & Maier

[57] ABSTRACT

A dye binding reagent for protein assay comprises Coomassie Brilliant Blue G-250 and an acid having a pKa of from 1 to 2. Upon addition of the reagent to a protein-containing solution, the attendant color change can be spectrophotometrically measured to quantitate even micrograms of protein. Furthermore, the reagent is applicable to a wide range of proteins and requires only about 2 minutes for measurement. Addition of an alcohol such as ethanol to the reagent further improves sensitivity.

23 Claims, 5 Drawing Figures

PROTEIN-ASSAY REAGENT AND METHOD

The invention described herein was made in the course of work under a grant or award from the Department of Health, Education and Welfare.

BACKGROUND OF THE INVENTION

1. Field of the Invention

The present invention relates to the detection and quantitative measurement of proteins.

2. Description of the Prior Art

Several methods are known for detecting the presence of protein in samples. These include the classical Lowry (Lowry, Oh. H., Rosebrough, N.J., Farr, A. L., and Randall R. J. (1951), *J. Biol. Chem.* 193, 265–275.) and biuret (Mokrasch, L. C., and McGilvery, R. W. (1956) *J. Biol. Chem.* 221, 909–917) methods which suffer from interference by many species commonly present in protein-containing solutions. Moreover, modified procedures for eliminating such problems are also disadvantageous since they are complicated and time consuming.

Another general protein analysis technique involves detection of a color change which occurs when a dye such as Orange G or bromo cresol green or purple becomes bound to a protein. These methods are based on the protein error phenomenon whereby proper buffering of the dye-containing reagent enables the normal pH sensitive color change of the dye to occur upon binding to the protein with no pH change. These methods are quite insensitive, detecting from mg to g of proteins; are only applicable to a limited number of proteins, typically to only a single one such as albumin, and are not applicable to protein quantitation in many important biological fluids such as urine. Moreover, for the dye binding technique, satisfactory sensitivity is achievable only by elimination of turbidity from the test mixture, for example by addition of surfactants (U.S. Pat. No. 3,884,637) and/or sequestering agents (U.S. Pat. No. 3,872,272) to prevent the precipitation of the dye/protein complex. A more sensitive dye binding technique does exist, but it requires precipitation and filtration and is therefore complicated and time consuming (Schaffner, W., and Weissmann, C. (1973) *Anal. Biochem.* 56, 502–514).

Dye/protein complex formation is also utilized for staining of proteins in gels used in electrophoresis. For example, the dye Coomassie Brilliant Blue G-250 in perchloric acid solution has been so used (Reisner, A. H. et al (1975) *Anal. Biochem.* 64, 509–516). However, these techniques involve precipitation of the colored protein/dye complex and are inapplicable to sensitive quantitative analysis of protein-containing solutions where spectrophotometric means are generally used for measurements. Consequently, a need exists for a more sensitive and rapid method for quantitative analysis of small amounts ($\mu$g) of protein.

SUMMARY OF THE INVENTION

Accordingly, it is the one object of the present invention to provide a reagent and method for its use in protein assaying which method is very sensitive, rapid and amenable to processing of a large number of samples.

It is another object of this invention to provide such a reagent and method which is applicable to many different types of proteins.

It is still another object of this invention to provide such a reagent and method which are not subject to interference from species normally present in protein-containing solutions.

Briefly, these and other objects of this invention as will hereinafter become clear have been attained by providing a reagent for use in a protein assay method which comprises the dye Coomassie Brilliant Blue and an acid having a pKa of from 1 to 2. A preferred embodiment in addition contains an alcohol such as ethanol.

BRIEF DESCRIPTION OF THE DRAWINGS

A more complete appreciation of the invention and many of the attendant advantages thereof will be readily attained as the same becomes better understood by reference to the following detailed description when considered in connection with the accompanying drawings, wherein.

DESCRIPTION OF THE PREFERRED EMBODIMENTS

The active color-changing ingredient in the reagent of this invention is the known dye Coomassie Brilliant Blue G-250 which has the formula:

While this dye has been used in the past for staining of proteins in electrophoresis by protein/dye complex precipitation as noted above, it has not been used for quantitative analysis of proteins in solution because of assumed lack of sensitivity and inappropriateness due to precipitation of the dye/protein complex. However, it has now been discovered that use of the G-250 dye in the appropriate acid medium results in a protein assay reagent having a sensitivity approximtely 100 times greater than those of the biuret and conventional dye binding techniques and about 3 to 5 times that of the Lowry method.

The acid ingredient must have a pKa of from 0 to 4, preferably from 1 to 2, and the resultant dye-containing solution should have a pH of from −1 to 1, preferably −0.5 to 0.5. Highly ionized acids such as perchloric acid, hydrochloric acid and sulfuric acid cannot be used in the reagent. Suitable acids include phosphoric acid and other acids with a pKa from 1–2 which do not result in protein precipitation. Typical candidates include periodic, phosphorous, selenic, sulfurous, maleic, oxalic, dichloroacetic acids and the like. Phosphoric acid is especially preferred.

The dye and the acid may be dissolved in any aqueous medium that does not contain surfactants, detergents, or exceedingly strong alkali, preferably water. The final concentration of the G-250 dye in the reagent should be from 0.001 to 0.1% (w/v), preferably from 0.005 to 0.05% (w/v); while that of the acid should be from 4 to 12% (w/v), preferably 7.5 to 9.5% (w/v). The order of addition of the dye and the acid is immaterial and both may be added directly to the aqueous medium or may be added to separate portions of the medium and thereafter mixed.

As previously mentioned, when this reagent is used for protein assay, sensitivities up to 100 times those obtained using conventional techniques are observed. While this represents a great advancement even over the Lowry method, a slight turbidity probably due to the dye/protein complex formation is present. It has been most surprisingly determined that addition of an alcohol, a well-known denaturing agent for proteins, i.e., an agent which is used to insolubilize proteins (see, for example, the Reisner reference cited above), can be used to remove this turbidity by solubilizing the resultant dye/protein complex. As a result, an approximate doubling in sensitivity of the reagent is achieved. Suitable alcohols include methanol, ethanol and propanol. Other appropriate alcohols are those with good water solubility which show no behavior as detergents. Especially preferred is ethanol. The concentration of the alcohol must be from 0.1% to 10% (w/v) preferably from 4 to 5% (w/v) for the dye and acid concentrations discussed A most unique property of the reagent of this invention is its applicability to a wide scope of different protein types. While most protein reagents can be used for only one or perhaps a few different proteins, the reagent of this invention displays its superior sensitivity to all serum proteins tested including albumin, globulin, hemoglobin, chymotrypsinogen A, cytochrome C and the like.

Another unique feature of the reagent is the small amount required for an assay. As opposed to the approximately 10 ml required for conventional assay of from 0 to 0.2 ml of sample containing from 0 to 200 $\mu$g of protein for the Lowry method or 0–10 mg for the biuret method, the present invention requires only from 1 to 5 ml of reagent formulated as described above. Generally, from 0.1 to 1 ml of the reagent of this invention should be used for every 0 to 25 $\mu$g of protein in the sample. Preferably, from 3 to 5 ml of the reagent of this invention, containing from 0.005 to 0.05% (w/v) of dye should be used for from 0 to 200 $\mu$ of protein in a sample, and from 0.5 to 1.5 ml of the reagent containing the same dye concentration should be used for from 0 to 10 $\mu$g of protein in a sample.

Other important advantages are derived from the fact that the reagent is stable and, as shown in Example 5, is not susceptible to interference from a large number of species commonly present in protein-containing samples. As can be seen there, only detergents have any appreciable effect. Moreover, timing of measurements is not critical since the color stability of the protein/dye complex is quite high, as also shown in the Examples.

The method of this invention involves addition of the reagent to a protein-containing sample, or vice versa. Detection of protein is effected by monitoring of the increase in absorbance at 595 nm due to formation of the dye/protein complex, using conventional instrumentation such as a Bausch and Lomb Spectronic 200 UV Spectrophotometer or any colorimeter capable of measuring radiation of a wavelength in the range of from 570 to 620 nm. The amount of protein is determined by comparison with preconstructed standard curves. The results are highly reproducible and accurate as shown in the Examples. Temperature is not critical. Typically, the assay is carried out at room temperature.

Because of the high sensitivity displayed, the reagent is capable of detecting amounts of protein as small as approximately from 0.5 to 1 $\mu$g in 0.1 ml of sample. Moreover, the time required for such accurate and sensitive determinations is less than about 2 minutes per sample in contrast to 30–40 minutes generally required for conventional assays. Consequently, the method of this invention is highly amenable to automation and analysis of large numbers of samples. The system has been automated using 0.005 ml of sample and 0.250 ml of reagent per assay. Standard deviation on 135 samples has been determined to be ± 0.6% of the mean.

Typical applications of the reagent and method of this invention include detection of protein in urine, serum, cerebrospinal fluid, foods, and any other biologically derived fluid or extract. Of great significance is the applicability of the reagent to protein detection in a urine environment. Conventionally, quantitation of protein in urine is subject to very significant interference from biological species contained therein. However, the use of this invention overcomes this defect. For example, the aforementioned automated assay was conducted using urine. 0.005 ml samples were used in the automated assay rather than 1.0 ml samples used in the conventional assay. The correlation indices of the conventional assay results with the dye binding method of this invention were good using replicate samples. Moreover, the reproducibility of the dye binding assay was exceedingly greater than that of the standard methodology. Since at the present time there is no satisfactory method for determining proteins in urine (results are typically accurate to only ± 5–50% of true values), this is a most significant result. Additionally, it has been determined that the method works well for protein assay in spinal fluids using 20–50 $\mu$samples of spinal fluid compared to the 0.5 to 1 ml spinal fluid samples required by conventional assays. Moreover, the sensitivity of the assay of this invention was very high in these tests. Thus, as with its applicability to urine analysis, this represents a significant advance since conventional protein assays in spinal fluid suffer from a lack of sensitivity. (For a comparison of the results of this invention, as applied to protein assay in urine and cerebrospinal fluid with the conventional turbidometric assay, see Example 6.)

As a mechanism for the reaction of the protein reagent with protein and the resulting color change, the following theory may be postulated. Coomassie Brilliant Blue G-250 exists in two different color forms, red and blue. The blue form of the dye is present in neutral and alkaline solution while the red form is present in markedly acid solution (pH 0–1). A similar type of acid-base reaction results when benzilic acid is subjected to strongly acid solution; the normally colorless benzilic acid turns brilliant red. This has been attributed to the formation of a carbanion on the organic acid. Perhaps the same type of mechanism exists for the normally blue colored Coomassie Brilliant Blue G-250. With this assumption made, the following is proposed as a principle on which the assay may work. The protein reagent is a carefully balanced form of the dye essentially at equilibrium between the red and blue forms. The reagent is somewhat brownish in appearance. As protein binds to the dye, the dye is brought into a different microenvironment thus being protected from the acid medium which gives the red color to the dye. This is somewhat substantial in that there is a tremendous loss in sensitivity of the assay by increasing the strength of the acid medium in which the reagent is made. The protein-dye complex does tend to aggregate as indicated in the Example on the stability of the color product. The presence of the indicated amount of ethanol in the reagent tends to keep the protein-dye complex from aggregating for a reasonable period of time; however, too much ethanol results in a marked shift to the blue form, i.e., change of the environment to one which is less polar. Then, it can be postulated that the mechanism of the assay is the binding of a carbanion form of the dye to a less polar environment of the protein. This perhaps also explains the effect of large quantities of detergent and of acetone on the assay, since these compounds are generally non-polar in nature and would tend to change the environment of the dye.

Finally, it should be noted that the mechanism of the protein/dye color change is not that of the conventional protein error type of dye reagents (U.S. Pat. No. 2,897,058). The functions of the acid and other ingredients such as alcohols in these reagents have no relation to those for these ingredients in this reagent, i.e., both the purposes and results are entirely different.

Having generally described the invention, a more complete understanding can be obtained by reference to certain specific examples, which are included for purposes of illustration only and are not intended to be limiting unless otherwise specified.

The materials and preparations used in the Examples are as follows

Reagents

Coomassie Brilliant Blue G-250 was obtained from Sigma, and used as supplied. 2-Mercaptoethanol was obtained from Sigma. Triton X-100 was obtained from Schwartz/Mann. Sodium dodecyl sulfate was obtained from BDH Chemicals Ltd., Poole, England. Hemosol was obtained from Scientific Products. All other reagents were of analytical grade or the best grade available.

Protein Preparation

Bovine serum albumin (2X crystallized), chymotrypsinogen A, and cytochrome C (horse heart) were obtained from Schwartz/Mann. Hemoglobin and human serum albumin were obtained from Nutritional Biochemicals Corporation. Protein solutions were prepared in 0.15 M NaCl. Concentrations were determined for bovine serum albumin, human serum albumin, chymotrypsinogen A and cytochrome C spectrophotometrically in a Bausch and Lomb Spectronic 200 UV spectrophotometer based on literature values for extinction coefficients of $\epsilon_{280}^{1\%} = 6.6, 5.3, 20$ and $17.1$, respectively. Hemoglobin solutions were prepared gravimetrically.

Preparation of Protein Reagent 100 mg Coomassie Brilliant Blue G-250 was dissolved in 50 ml 95% ethanol. To this solution 100 ml 85% (w/v) phosphoric acid was added. The resulting solution was diluted to a final volume of 1 liter. Final concentrations in the reagent were 0.01% (w/v) Coomassie Brilliant Blue G-250, 4.7% (w/v) ethanol, and 8.5% (w/v) phosphoric acid.

Protein Assay (standard method)

Protein solution containing from 10 to 100 µg protein in a volume of up to 0.1 ml was pipetted into 12 × 100 mm test tubes. The volume in the test tube was adjusted to 0.1 ml with appropriate buffer. 5 ml of protein reagent was added to the test tube and the contents mixed either by inversion or vortexing. The absorbance at 595 nm was measured after 2 minutes and before 1 hour in 3 ml cuvettes against a reagent blank prepared from 0.1 ml of the appropriate buffer and 5 ml of protein reagent. The weight of protein was plotted against the corresponding absorbance resulting in a standard curve used to determine the protein in unknown samples.

Micro Protein Assay

Protein solution containing from 1 to 10 µg protein in a volume of up to 0.1 ml was pipetted into 12 × 100 mm test tubes. The volume in the test tubes was adjusted to 0.1 ml with the appropriate buffer. 1 ml of protein reagent was added to the test tube and the contents mixed as in the standard method. Absorbance at 595 nm was measured as in the standard method except in 1 ml cuvettes against a reagent blank prepared from 0.1 ml of the appropriate buffer and 1 ml of protein reagent. Standard curves were prepared and used as in the standard method.

Cuvette Cleaning

A difficulty observed in performing the assay is the tendency of the protein-dye complex in solution to bind to quartz cuvettes. This results in a blue colored cuvette. (This does not occur with glass or plastic cuvettes.) The amount of binding is negligible as far as assay readings are concerned, i.e., less than 1% error, as indicated by the standard deviation of triplicate assays in the reproducibility Example. The blueness of the cuvettes after assay will present problems in other uses of the cuvettes so the following directions for cleaning the blue complex from cuvettes should be followed.

Method 1: Rinse cuvettes with concentrated glassware detergent followed by water and acetone. (Gives immediate removal)

Method 2: Soak cuvettes in 0.1 M HCl. (Removes complex in a few hours)

EXAMPLE 1

Reproducibility, Sensitivity and Linearity of the Assay

Figure 1:
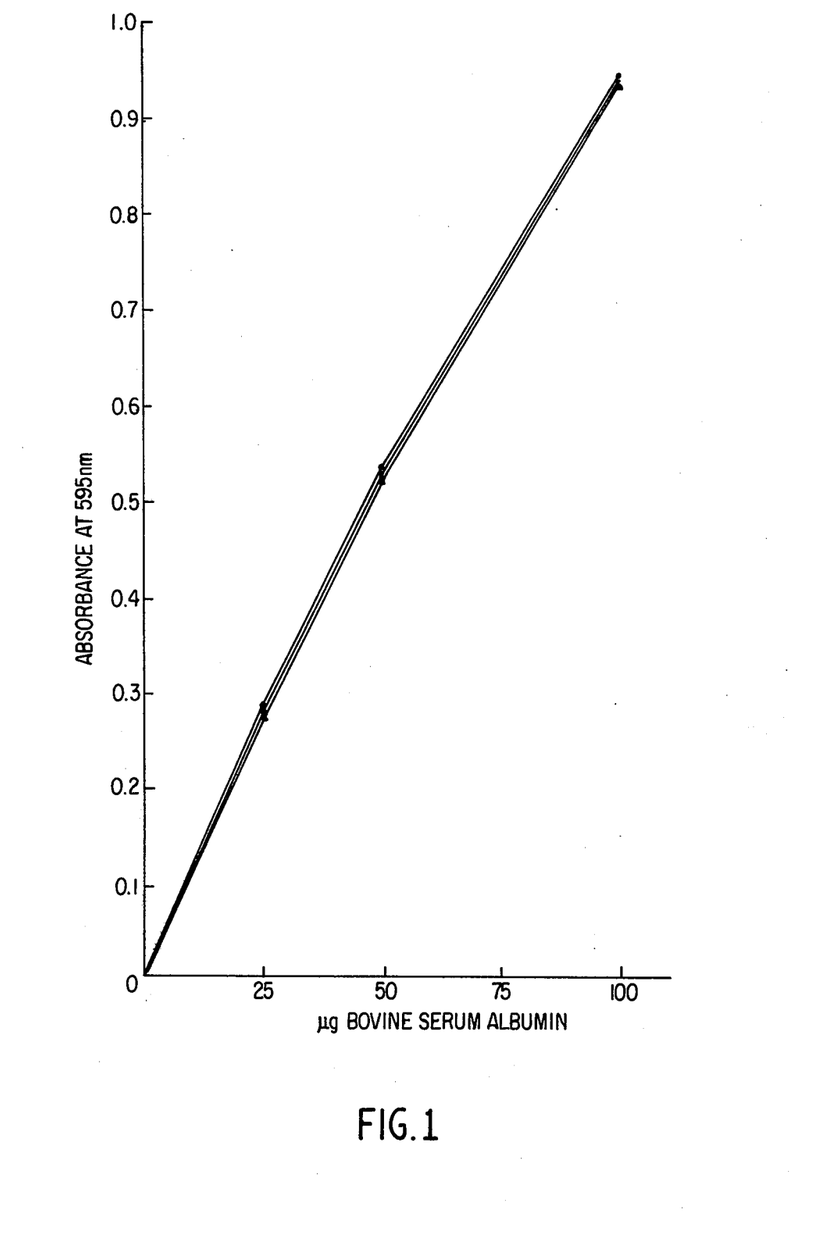
FIG. 1 illustrates the reproducibility and sensitivity of a bovine serum albumin assay by the protein dye binding method of this invention.

Triplicate assays of bovine serum albumin as a standard gave the plot shown in FIG. 1. As seen from the graph, the assay is quite reproducible. Statistical analysis gave a standard deviation of 1.2% of mean value for the assay. The graph also shows that there is extreme sensitivity in the assay, with a 25 µg sample giving an absorbance change of 0.275 O.D. units. This corresponds to 5 µg protein/ml in the final assay volume. The assay system has a nonlinear response as can be seen from the graph. The source of the nonlinearity is in the reagent itself since there is an overlap in the spectrum of the two different color forms of the dye. The background value for the reagent continually decreases as more dye is bound to protein. This presents no real problem in practice since the degree of curvature is only slight. If the assay is run with a set of standards, and the unknowns measured against the response curve of the standards instead of calculated by Beer's Law, there is no difficulty in obtaining highly satisfactory results.

EXAMPLE 2

Accuracy of the Assay

Figure 2:
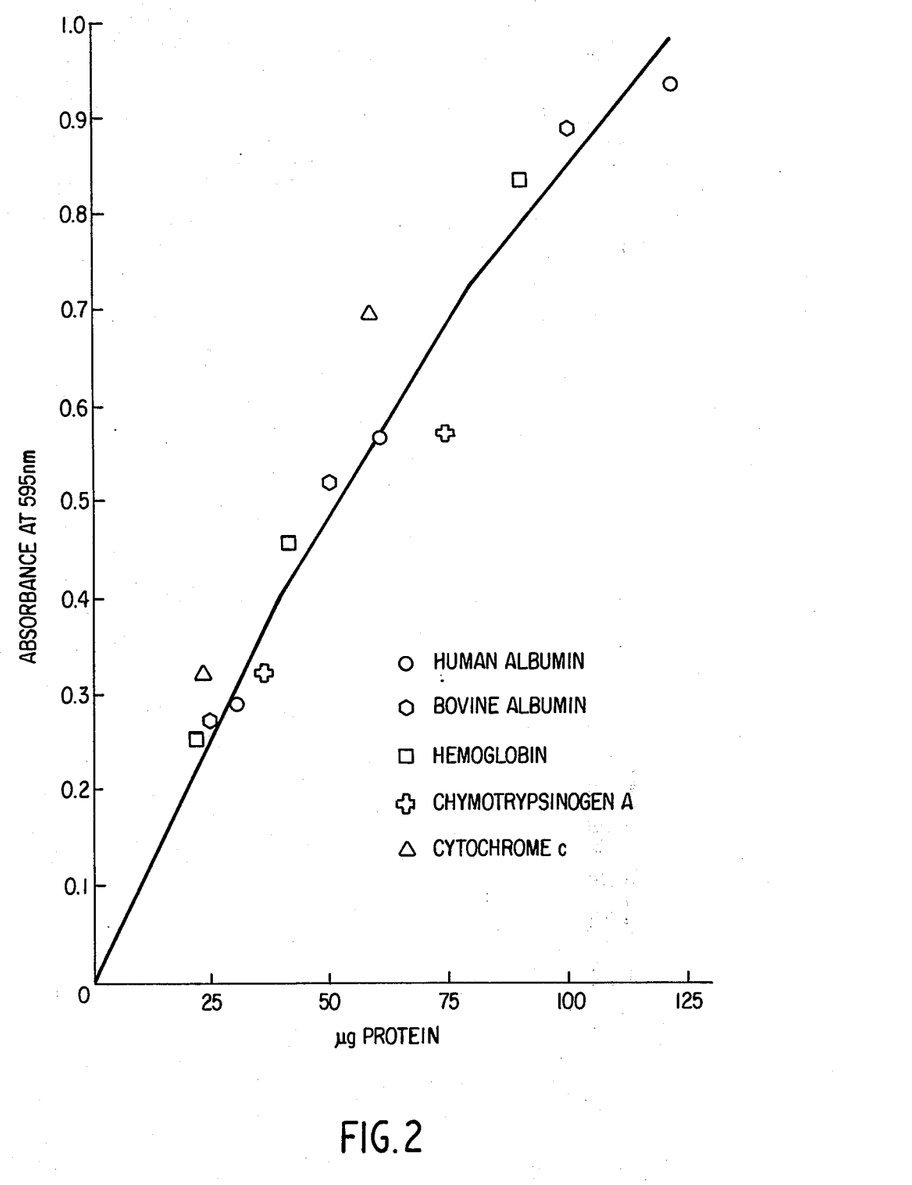
FIG. 2 shows the protein dye binding response pattern of this invention for various proteins.
Figure 3:
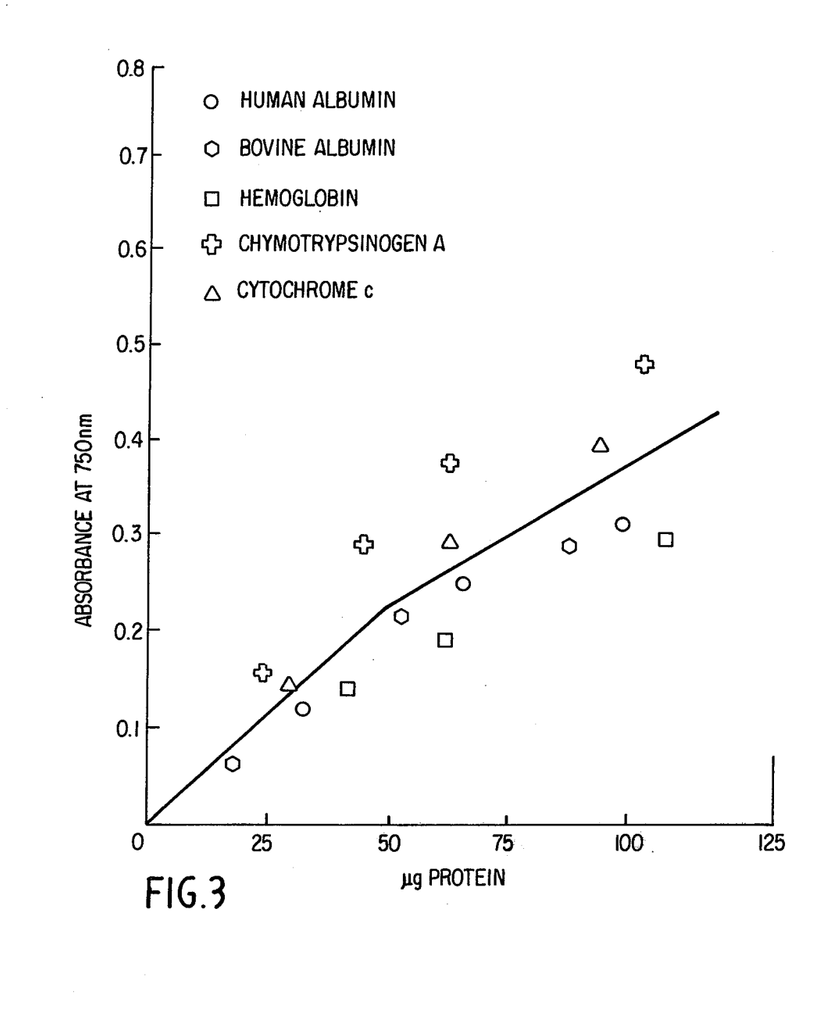
FIG. 3 shows the prior art Lowry response pattern for various proteins.

FIG. 2 shows the individual responses of various proteins assayed in the system. There is a scattering of points around the line drawn in the graph. The scattering is believed to be a multifaceted function due to difficulties in determining the exact amount of protein present in a given sample because of variations in extinction coefficients in the literature, the methods used to determine the exact amount of protein employed in measuring extinction coefficients, and some degree of variation in the efficiency of dye binding to various proteins. obtained from Lowry assays of the same proteins. FIG. 3 shows the pattern The degree of scatter in the protein response to the Lowry assay is similar to that shown for the dye-binding assay presented here. The sensitivity of the Lowry method is an absorbance of 0.110 O.D. units for the 25 $\mu g$ standard corresponding to 8 $\mu g$protein/ml of final assay volume. By calculation then, the dye binding assay of this invention is approximately four times more sensitive than the Lowry assay. The degree of scatter around the Lowry assay plot also demonstrates the difficulty in establishing a quantitative value for a protein in standard solution.

EXAMPLE 3

Stability of the Protein-Dye Complex Color

Figure 4:
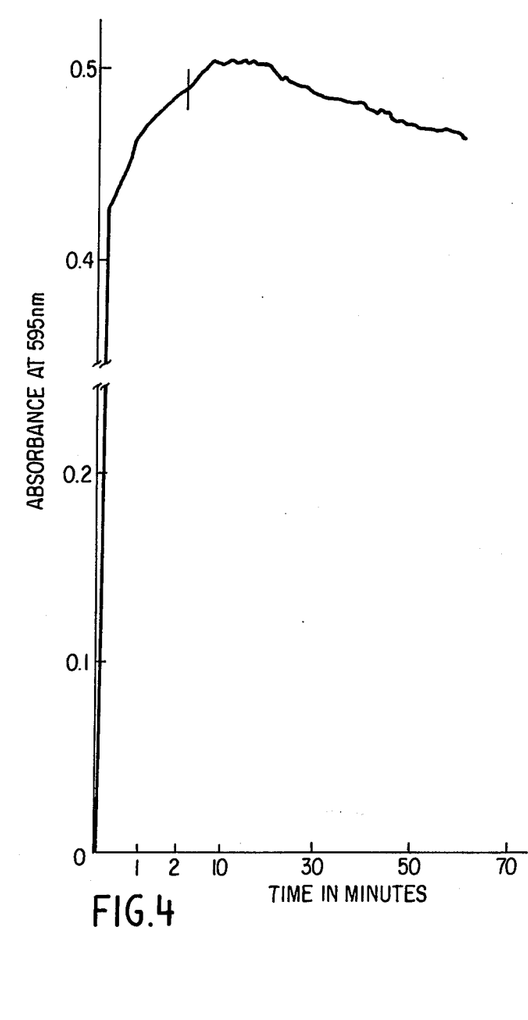
FIG. 4 illustrates the protein-dye complex formation rate and color stability of this invention.

FIG. 4 shows the rate of formation of protein-dye complex in the assay system and the stability of the color complex. The absorbance was monitored at 7.5 second intervals for 2 minutes and then at 1 minute intervals for a period of 1 hour. As seen from the graph, the color development is essentially complete at 2 minutes, and remains stable plus or minus 4% for a period of 1 hour. Since the protein-dye complex has a tendency to aggregate with time, there is a decrease in color after this period simply by the physical removal of the protein-dye complex from solution. If very precise determinations are required, precautions can be taken to read the absorbance of samples during one of the flatter portions of the color stability curve between 5 and 20 minutes after reagent addition. This still gives ample time to read a relatively large number of samples.

EXAMPLE 4

Micro Assay System Sensitivity

Figure 5:
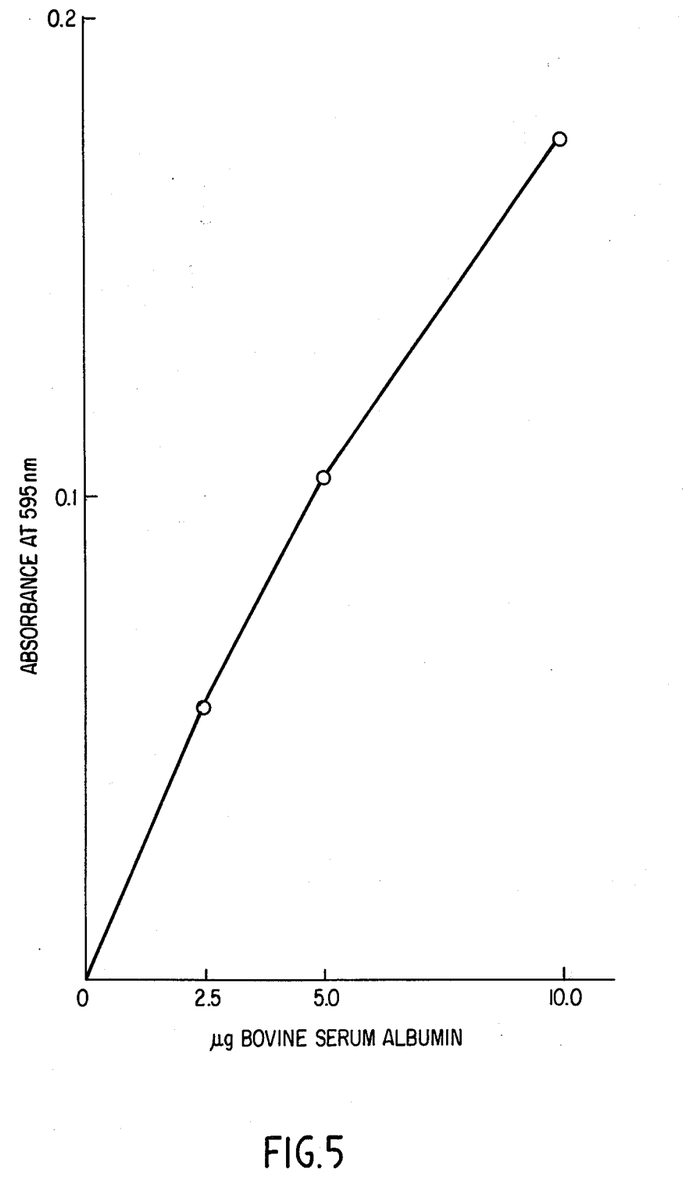
FIG. 5 shows the response pattern for bovine serum albumin in a micro assay of this invention.

FIG. 5 shows the results of performing the micro assay using bovine serum albumin as the standard. The degree of curvature is similar to that found in the standard assay. There is a loss in protein-dye complex response as compared with the standard assay, i.e., 5 $\mu g$ protein/ml gives an absorbance change of 0.1 vs 0.27 in the standard assay. Perhaps this results from increased dilution of the protein reagent.

EXAMPLE 5

Interference by Non-Protein Components

As indicated in the introduction, there is some interference in the assay system by strongly alkaline buffering agents. This may be overcome by running the appropriate buffer controls and subtracting the value for the control either mathematically or spectrophotometrically. A wide spectrum of components was tested for effects on the protein dye binding assay as shown in Table 1. Results were determined by performing the standard assay including 0.1 ml of each substance.

TABLE I

EFFECT OF VARIOUS LABORATORY REAGENTS ON COOMASSIE BRILLIANT BLUE-G-250 PROTEIN COMPLEX ASSAY

| Substance | Change in O.D. 595nm | Equivalent $\mu g$ BSA |
| --- | --- | --- |
| 1 M KCl | 0.000 | 0.00 |
| 5 M NaCl | 0.000 | 0.00 |
| 1 M MgCl$_2$ | 0.000 | 0.00 |
| 2 M Tris | 0.026 | 2.34 |
| 0.1 M EDTA | 0.004 | 0.36 |
| 1 M (NH$_4$)$_2$SO$_4$ | 0.000 | 0.00 |
| 99% Glycerol | 0.012 | 1.08 |
| 1 M 2-mercaptoethanol | 0.004 | 0.36 |
| 1 M sucrose | 0.013 | 1.17 |
| 95% ethanol | 0.000 | 0.00 |
| Acetone | 0.069 | 6.21 |
| 5% Phenol | 0.046 | 4.14 |
| 0.1% Triton X-100 | 0.013 | 1.17 |
| 1% Triton X-100 | 0.590 | 53.10 |
| 0.1% sodium dodecyl sulfate | 0.011 | 0.99 |
| 1% sodium dedecyl sulfate | 0.495 | 44.55 |
| 0.1% Hemosol | 0.004 | 0.36 |
| 1% hemosol | 0.108 | 9.72 |

A lack of effect on the assay by magnesium chloride, potassium chloride, sodium chloride, ethanol and ammonium sulfate was observed. The small effects due to Tris, acetic acid, 2-mercaptoethanol, sucrose, glycerol, EDTA, and trace quantities of the detergents, Triton X-100, sodium dodecyl sulfate, and Hemosol, can be easily eliminated by running the proper buffer control with the assay.

Additionally, it has been determined that bilirubin which markedly interferes with the conventional turbidometric assay and urea, ammonia and uric acid which markedly interfere with the conventional biuret and Lowry assays, have little or no effect on the dye binding assay of this invention. The presence of large quantities of the detergents should be avoided.

EXAMPLE 6

Results of Protein Assay on Cerebrospinal Fluid and Urine

When cerebrospinal fluid was assayed for protein by the standard turbidometric assay and by the dye-binding assay of this invention, virtually identical results were obtained. The turbidometric assay requires from 0.5 to 1.0 ml of cerebrospinal fluid, while the dye-binding assay of this invention requires only 0.05 $\mu g$.

When urine was assayed for protein by the standard turbidometric assay and by the dye-binding assay of this invention, comparable results were obtained.d The reproducibility of the dye-binding assay was within the standard deviation of 1.2% as reported in Example 1. The variability of the turbidometric assay was from 5 to 50% of mean value depending upon the range in which the assay was performed.

Having now fully described the invention, it will be apparent to one of ordinary skill in the art that many changes and modifications can be made thereto without departing from the spirit or scope of the invention as set forth herein.

What is claimed as new and intended to be covered by letters patent is:

1. A reagent for use in protein assay which comprises the dye:

and an acid having a pKa of from 0 to 4.

2. The reagent of claim 1, wherein the acid has a pKa of from 1 to 2.

3. The reagent of claim 1, wherein the acid is phosphoric acid.

4. The reagent of claim 1, wherein the pH of the resultant solution is from −1 to 1.

5. The reagent of claim 1, wherein the concentration of said dye is from 0.001 to 0.1% (w/v) and of said acid is from 4 to 12% (w/v).

6. The reagent of claim 1, which further comprises an alcohol.

7. The reagent of claim 6, which contains from 0 to 10% (w/v) of said alcohol.

8. The reagent of claim 6, wherein said alcohol is ethanol.

9. The reagent of claim 6, which contains from 0.005 to 0.05% (w/v) of said dye, from 7.5 to 9.5% (w/v) of phosphoric acid and from 4 to 5% (w/v) of ethanol.

10. A method of assaying protein which comprises mixing a reagent comprising the dye and an acid having a pKa of from 0 to 4 and a protein-containing sample and observing the resultant color change.

11. The method of claim 10, wherein said change is monitored spectrophotometrically at a wavelength of from 570 to 620 nm.

12. The method of claim 10, wherein from 0.1 to 1 ml of said reagent is added for up to 25 μ of protein in said sample.

13. The method of claim 10, wherein the protein is selected from the group consisting of albumin, hemoglobin, globulin, chymotrypsinogen A and cytochrome C.

14. The method of claim 10, wherein the protein containing sample is urine.

15. The method of claim 10, wherein the protein-containing sample is spinal fluid.

16. The method of claim 10, wherein the acid is phosphoric acid.

17. The method of claim 10, wherein the pH of the resultant solution is from −1 to 1.

18. The method of claim 10, wherein the concentration of said dye is from 0.001 to 0.1% (w/v) and of said acid is from 4 to 12% (w/v).

19. The method of claim 10, wherein said reagent further comprises an alcohol.

20. The method of claim 19, wherein said reagent contains from 0 to 10% (w/v) of said alcohol.

21. The method of claim 19, wherein said alcohol is ethanol.

22. The method of claim 10, wherein an automated analyzer is employed.

23. A method of assaying protein which comprises mixing a reagent which contains from 0.005 to 0.05% (w/v) of from 7.5 to 9.5% (w/v) of phosphoric acid and from 4 to 5% (w/v) of ethanol, and a protein containing sample and observing the resultant color change.

* * * * *

UNITED STATES PATENT OFFICE
CERTIFICATE OF CORRECTION

Patent No. 4,023,933      Dated May 17, 1977

Inventor(s) Marion M. Bradford et al.

It is certified that error appears in the above-identified patent and that said Letters Patent are hereby corrected as shown below:

Column 1, line 27, "protein error should read -- "protein error" --.

Column 3, line 37, add "above." to end of sentence.

Column 3, line 57, change "μ" to -- "μg" --.

Column 4, line 50, change "μsamples" to -- μl samples --

Column 5, line 33, add quotation marks before and after "protein error".

Column 7, lines 22 and 23, delete "FIG. 3 shows the pattern" from line 23 and insert it into line 22 after the word "proteins." so that it begins a new sentence reading -- FIG.3 shows the pattern obtained from Lowry-- etc.

Column 8, line 63, change "obtained.d" to -- obtained. --

Claim 12, line 2, change "μ of protein" to -- μg of protein --

Signed and Sealed this

Twentieth Day of June 1978

[SEAL]

Attest:

RUTH C. MASON
*Attesting Officer*

DONALD W. BANNER
*Commissioner of Patents and Trademarks*